(12) United States Patent
Wei et al.

(10) Patent No.: US 8,933,291 B2
(45) Date of Patent: Jan. 13, 2015

(54) DEHYDRATION SENSORS HAVING BUFFERED INKS

(75) Inventors: Ning Wei, Roswell, GA (US); Xuedong Song, Alpharetta, GA (US); Ronnie L. Phillips, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 507 days.

(21) Appl. No.: 12/858,234

(22) Filed: Aug. 17, 2010

(65) Prior Publication Data
US 2012/0046628 A1   Feb. 23, 2012

(51) Int. Cl.
| A61F 13/15 | (2006.01) |
| G01N 21/75 | (2006.01) |
| G01N 31/22 | (2006.01) |
| G01N 33/52 | (2006.01) |
| G01N 21/80 | (2006.01) |
| A61F 13/42 | (2006.01) |
| G01N 21/81 | (2006.01) |
| G01N 21/77 | (2006.01) |

(52) U.S. Cl.
CPC .............. *G01N 21/80* (2013.01); *A61F 13/42* (2013.01); *G01N 21/81* (2013.01); *G01N 2021/7759* (2013.01)
USPC .......................................... 604/361; 422/420

(58) Field of Classification Search
USPC .............. 604/361, 358; 422/420–424; 436/2, 436/164, 169
See application file for complete search history.

(56) References Cited

U.S. PATENT DOCUMENTS

| 3,552,928 | A | * | 1/1971 | Fetter ............................ 422/422 |
| 4,076,502 | A | * | 2/1978 | Dugle et al. ..................... 435/14 |
| 4,318,709 | A |   | 3/1982 | Falb et al. |
| 4,376,827 | A |   | 3/1983 | Stiso et al. |
| 5,403,744 | A | * | 4/1995 | Zimmerle ......................... 436/2 |
| 7,159,532 | B2 | * | 1/2007 | Klofta et al. ................... 116/206 |
| 8,623,292 | B2 | * | 1/2014 | Song et al. ..................... 422/420 |
| 2007/0199165 | A1 | * | 8/2007 | Sun et al. .......................... 8/552 |
| 2008/0103414 | A1 | * | 5/2008 | Song .............................. 600/573 |
| 2010/0159599 | A1 |   | 6/2010 | Song et al. |
| 2010/0159611 | A1 |   | 6/2010 | Song et al. |
| 2011/0152805 | A1 | * | 6/2011 | Gil ................................ 604/361 |
| 2011/0281988 | A1 | * | 11/2011 | Tanoue et al. .................. 524/386 |

* cited by examiner

*Primary Examiner* — Lynne Anderson
*Assistant Examiner* — Bradley Philips
(74) *Attorney, Agent, or Firm* — Denise L. Stoker; Vincent T. Kung

(57) ABSTRACT

A dehydration sensor having a stable, printable, buffered-ink composition that enables one to miniaturize the detection zone and permits both buffer and indicator dye to be applied in the same area of a detection zone, without need for a conventional, large buffer pad region.

13 Claims, 6 Drawing Sheets

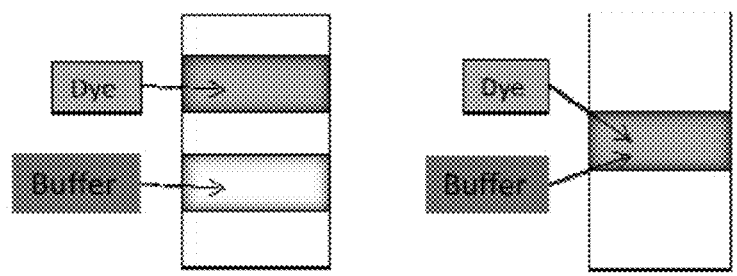
FIG. 2A          FIG. 2B
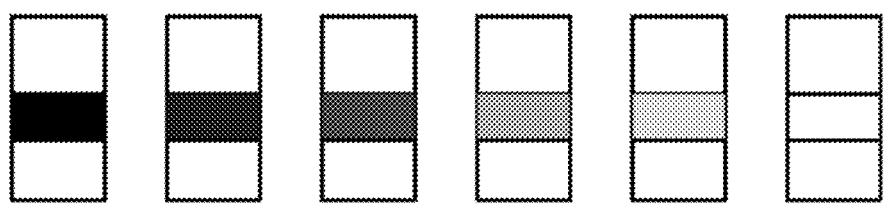
USG:  1.002   1.008   1.014   1.020   1.025   1.035
FIG. 3

DEHYDRATION SENSORS HAVING BUFFERED INKS

FIELD OF INVENTION

The present invention pertains to dehydration indicators for use in an absorbent, personal-care product. In particular, the invention describes a dehydration sensor which incorporates buffered inks.

BACKGROUND

Dehydration is the depletion of fluids, mostly water, and associated electrolytes from the body. Normally, a person's daily, total fluid amount is regulated to be within about ±0.02% of body weight, and water in the body may comprise approximately 63% of the entire body mass. A balance of bodily fluids is achieved and maintained by matching the input and excretion of liquid from the body, and an imbalance in fluids can be linked to either dehydration or hypohydration.

Although dehydration can occur in persons of all ages, it is of particular concern for either the infirm, elderly, or infants. Dehydration can pose serious consequences to a dehydrated person if not cared for properly. These consequences can include muscle cramps, dizziness, fainting, and even death in extreme cases. Loss of body fluids in amounts of less than about 2-5% body mass have been associated with reduced heat dissipation, loss of cardiovascular function, and decreased physical stamina. At the onset of dehydration, the increase of plasma osmolarity (solute concentration in plasma) causes a sensation of thirst. This early warning sign, however, is often missed in situations where the person cannot adequately communicate with their caregiver, such as infants and the disabled or elderly. People who are incontinent also have high chance of missing this dehydration sign since they are more likely to restrict their liquid intake to avoid the chances of embarrassing accidents. Consumers such as these or their caretakers have a strong interest in choosing personal care products that include dehydration indicators.

Specific gravity of an individual's urine is a routinely measured means of evaluating the relative hydration status of the individual. Determination of urine volume and electrolyte concentrations can aid in monitoring whether the individual's body fluid amounts are in balance. Urine specific gravity (USG) refers to the ratio of the density of urine to the density of water. USG is affected mainly by the solids and ions in urine. USG correlates proportionally with the solid concentration and ion concentration of urine. USG normally ranges from 1.002 to 1.030. It is accepted that USG<1.020 is considered to be well hydrated, USG between 1.020 and 1.025 is considered to be semi-dehydrated and USG>1.025 is considered to be severely dehydrated. USG can be measured by an instrument such as either a urinometer or urine test dipsticks or strips. Modern dipsticks are commonly based on lateral flow assay technology. Three major methods, namely refractometry, hydrometry and reagent strips, are commonly used for USG measurements. Although refractometry and hydrometry are very accurate, they require special instruments and trained persons to operate.

Over the years, various manufacturers have attempted different methods to improve the performance of the dipsticks for specific gravity, such as different formulations to increase sensitivity and specificity. Problems, however, persist for all the commercially available dipsticks. A major problem is that the user has to read a change in color within a few brief minutes after dipping in the sample because the color development is not stable under test conditions. The signals that one may observe outside of the time window are often inaccurate, hence normally invalid. For some analyte tests, such as ion concentration in urine (i.e., specific gravity for dehydration), a certain time period is needed before a signal is fully developed and a valid reading can be achieved. This situation may not be a problem for a test that a user can constantly monitor; however, it becomes a problem when constant monitoring of the test is not feasible and sample introduction time is uncertain. For instance, it is difficult, if not impossible, to predict accurately when a baby or incontinent adult will urinate to provide a sample for an assay device in a diaper or other personal care product. Therefore, the assay device requires a validation mechanism to make sure that a reading is within the valid reading time window.

In recent years, reagent strips have become more popular, particularly in the over-the-counter and point-of-care markets, mainly due to their low cost and ease of use. In general, conventional reagent strips change color in response to the ionic strength of a urine sample. The ionic strength of urine is a measure of the amount of ions present in the urine. The USG is proportional to the ionic strength of the urine. Therefore, by assaying the ionic strength of the test sample, the USG can be determined indirectly and semi-quantitatively by correlating the ionic strength of the urine to the USG.

Conventional reagent strips are usually made in such a way that all the relevant reagents are diffusively immobilized together on a small porous zone on the strip. A sample of urine is then applied to the zone or the entire strip is dipped in the urine sample and then pulled out quickly to allow color to develop. Examples of such conventional reagent strips are described in U.S. Pat. No. 4,318,709 to Falb et al. and U.S. Pat. No. 4,376,827 to Stiso et al.

U.S. Pat. No. 4,318,709 to Falb et al. and U.S. Pat. No. 4,376,827 to Stiso et al., both of which are incorporated by reference herein, describe the polyelectrolyte-dye ion exchange chemistry utilized in conventional test strips for measuring USG. In such conventional test strips, ions present in urine induce an ion-exchange with a polyelectrolyte, thereby introducing hydrogen ions into the urine. The change in hydrogen ion concentration is detected by a pH indicator.

However, conventional reagent strips for USG measurement suffer from major shortcomings, particularly for over-the-counter and point-of-care markets. For instance, conventional reagent strips have a limited reading window because the signal produced by such strips begins to change only a short period of time after sample application. Signal change can be caused by reagent leaching (the result of diffusively immobilized reagents) and sample evaporation. Unless the strips are analyzed shortly after application of the sample, the signal change can lead to erroneous test results. Furthermore, because the reagents in conventional strips are typically water soluble, the strips must also be pulled out quickly from the urine sample to prevent the reagents from leaching into the sample. In addition, conventional reagent strips are often designed for only a single urine sample application. Multiple urine insults can lead to erroneous test results making such strips unsuitable for applications in absorbent articles where multiple urine insults cannot be controlled. Finally, conventional reagent strips do not provide a way for a user to know if the test has been performed correctly or if enough sample has been applied.

Thus, an unsatisfied need exists for an assay device that can provide such assurance to caregivers in a cost effective way to help monitor a user's hydration status.

SUMMARY OF THE INVENTION

The present invention describes an ink-based approach to create a dehydration sensor with a unitary assay format for measuring specific gravity of urine, where a dye formulation and buffer formulation are deposited in the same area or zone of a cellulosic substrate. These sensors require much fewer steps for construction, exhibit greater sensitivity and stability, utilize less reagent materials which make them much more economical, and can provide a sharp or gradual color transition. Further optimized formulations of the buffer may be developed to target a specific cut-off point between a hydrated and dehydrated state.

The dehydration sensor has: a porous substrate, with a buffered ink system that is directly deposited on a portion of the substrate. The buffered ink system is composed of either a) 0.5-30 wt. % of a weak polymeric acid, or b) 0.5-12 wt. % of a weak polymeric base, or c) a combination of 0.5-30 wt. % of the weak polymeric acid and 0.5-12 wt. % of the polymeric base, 0.5-70 wt. % of a polymeric stabilizer, and a surfactant; and a pH-sensitive dye. Alternatively, the percentage of acid may range between about 0.5% to about 15%, or more typically between about 1% to about 12%, or 2% to about 8%. And, alternatively, the amount of weak base may be in a similar range of between about 0.5% to about 10%. The composition permits one to be able to apply or print the buffered ink easily on a porous substrate adapted for lateral flow assays, while maintaining its stability and color development accuracy.

In another aspect, the present invention also relates to an absorbent article incorporating a lateral flow-based dehydration sensor, as described above, for measuring the specific gravity of urine and thus monitoring relative hydration or dehydration. The article includes a first inner layer that is proximal to the user's body, an absorbent core, and a second outer layer forming an outer casing that is away from the user's body. The dehydration sensor is situated near an area of the inner layer that will be subjected to insult of urine, and which will itself be insulted either directly or by wicking or capillary transport of the urine to the assay device. The dehydration sensor should be positioned such that a user or caretaker can easily observe a color signal change in either the detection zone and/or control zones. As above, the assay device has a first substrate with a porous matrix adapted for conducting lateral flow. The substrate has a sample deposit zone, and a buffer pad with a detection zone, and a control zone situated on a wicking pad downstream of the detection zone. In some embodiments, a flow-rate control zone, such as described in U.S. Patent Application Publication Nos. 2010/0159611 A1 or 2010/0159599 A1, the contents of which are incorporated herein by reference, is located between the detection zone and control zone. The flow-rate control zone regulates an amount of time needed for development and appearance of a visual signal in the control zone of the wicking pad until a color transition in the detection zone of the buffer pad attains color stability. Each of the several zones is in fluidic communication with each other either directly or indirectly by an adjacent component. Examples of absorbent articles may include, diapers, adult incontinence products, or personal or feminine hygiene products, or absorbent pads for medical or hospital uses.

Alternatively, the invention describes an insert for a garment (e.g., underwear) or absorbent personal care product, the insert comprising a dehydration sensor, as described above, having: a substrate having a porous matrix in fluidic communication with a buffer pad, wicking pad. The buffer pad has a detection zone with a buffered ink system, which is directly deposited on the portion of the substrate. The buffered ink system is composed of either 0.5-30 wt. % of a weak polymeric acid or 0.5-10 wt. % of a weak polymeric base, or a combination of 0.5-30 wt. % of the weak polymeric acid and 0.5-10 wt. % of the polymeric base, 0.5-70 wt. % of a proton-exchange hydrogen bonding neutral buffer bridge, and a surfactant; and a pH-sensitive dye. In some embodiments, one can have a flow-rate control zone situated between the buffer pad and wicking pad, as described above. An underlying substrate supports each of the zones and secures them together in an integrate device.

Additional features and advantages of the present three-dimensional sensor or assay device and associated absorbent articles containing such a sensor will be described in the following detailed description. It is understood that the foregoing general description and the following details description and examples are merely representative of the invention, and are intended to provide an overview for understanding the invention as claimed.

BRIEF DESCRIPTION OF FIGURES

FIGS. 2A and 2B, are schematic representations of a dehydration sensor according to the present invention. In FIG. 2A the pH-sensitive dye and buffer zone are separate areas on a substrate, while in FIG. 2B the dye and buffer zones overlap one another in the same physical area on the substrate.

FIG. 3 is a schematic representation of the relative change in color appearance in the detection zone of a dehydration sensor according to the present invention. From left to right, the color intensity manifest in the detection zone changes as the specific gravity of urine (USG) increases.

FIG. 4F shows the ink spots of sample 6, before treatment with urine, and FIG. 4G show the color development of sample 6 in the spots after contact with urine.

DETAILED DESCRIPTION OF THE INVENTION

Figure 1:
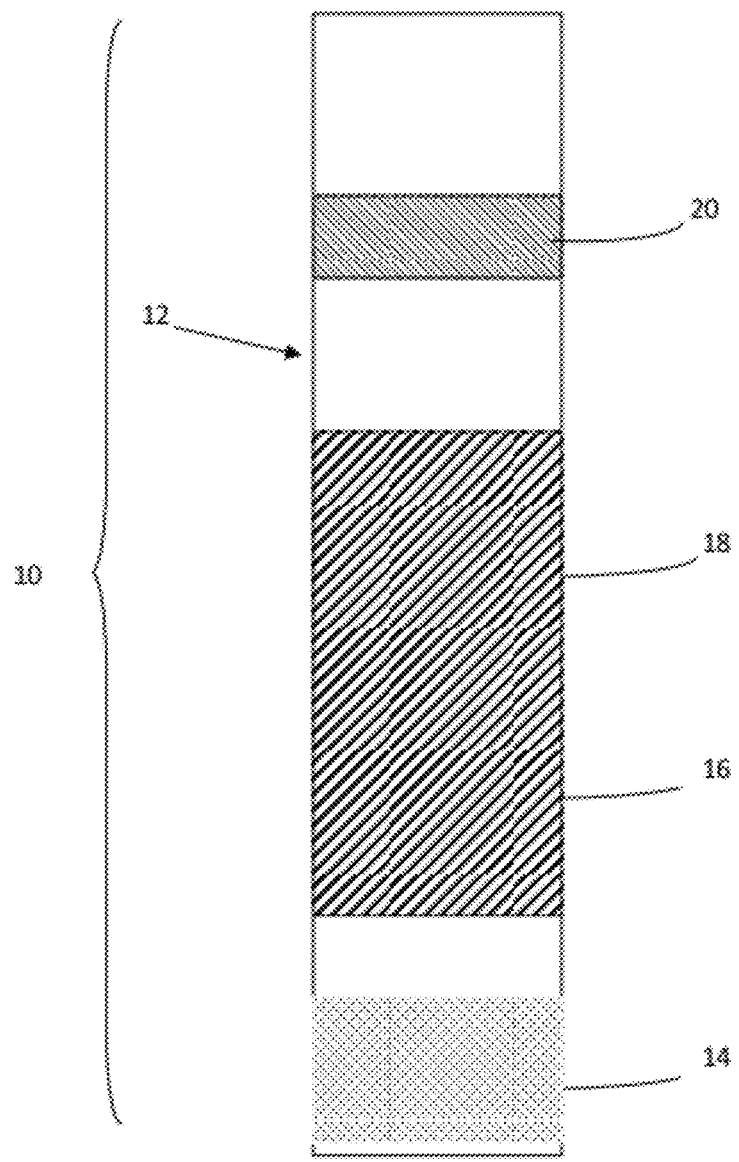
FIG. 1 is a face-on schematic representation of a lateral flow dehydration device having a number of different functional zones.

As dehydration is one of the leading causes of morbidity and mortality in children throughout the world and accounts for as much as 30% of worldwide deaths among infants and toddlers, there is a strong need to develop an indicator that is capable of semi-quantitatively determining hydration status.

Conventional urine testing devices, such as dipsticks or test strips, operate by dipping the dipstick in a urine sample and pulling it out quickly, and then read the resultant color that can be compared with a color scale. Typically these test strips have a short reading window, typically about or less than two minutes, and do not have any user feedback mechanism. Recently, an improved hydration monitoring and test format was developed, as described in U.S. patent application Ser. No. 11/956,428, the contents of which are incorporated herein by reference. Unlike previously developed lateral flow hydration test formats, the hydration monitoring and assay device according to U.S. patent application Ser. No. 11/956,428 has a reading window with a much longer duration of at least about 2 hours, typically about 4-6 hours or greater, with stable color signal and a user feedback zone to indicate a sample volume and sample contact with the test zone. The long reading window and long term stability of the color signal and user feedback mechanism are important features for an over-the-counter (OTC) test format, in particular, for a test in a personal care product, where constant monitoring is not practical.

The present invention builds upon the successes of other lateral flow test formats, such as described in U.S. patent application Ser. Nos. 11/956,428, or 12/338,673, the contents of which are incorporated herein by reference, and addresses some of their shortcomings. The present invention retains all the advantages of a lateral flow device for dehydration monitoring, while providing for a dehydration sensor that can respond to a broad USG range and stable distinctive color changes.

The invention discloses a dehydration sensor that utilizes a buffer system composed of both weak acids and weak bases. The combined buffer system has a much higher buffer capacity compare to the single buffer component systems, thus only a small quantity of buffer is needed to achieve similar efficacy as to conventional assay devices. Conventional dehydration sensors require a relatively large area of the substrate to serve as a buffer pad so that they can optimize their sensitivity. Unlike conventional dehydration sensors that are prepared using a single buffer, the present invention is much more sensitive to the changes in ion concentration in urine sample. This feature permits one to create dehydration sensors that do not, the combined buffer system of the present invention enables one to employ a much smaller substrate (i.e., at least one-half or one-third the size of previous buffer pads). This advantage allows one to deposit or print the sensing components (i.e., dye and buffer) on a single spot due to its significantly increased buffer capacity. The spot can have a linear or diameter/cross-sectional dimension of about 1 mm to about 30 mm, more typically about 2 or 3 mm to about 20-25 mm, or about 4 or 5 mm to about 10 mm or 12-17 mm, and preferably between about 1-5 mm, inclusive of various combinations of ranges therein. In comparison a conventional buffer pad commonly requires linear dimensions of about 3-4 cm×28-30 cm or an area of about 84-120 cm². One does not need to have a relatively long buffer pad section between the sample deposit zone and the detection zone, which allows the urine to travel to the detection zone. Hence, an advantage of the present invention is its ability to maintain good sensitivity to ion concentrations in urine while allowing one to miniaturize the buffer pad section of the sensor.

Furthermore, in the present invention, the pH indicating dyes can be directly immobilized to a cellulosic buffer pad, which eliminates a need for a protective film or cover over the detection zone. This advantage simplifies and reduces costs for the manufacture of the dehydration sensor device, eliminating additional fabrication steps. For instance, compared to some conventional dehydration sensors included a dye on a nylon carrier pad to support the dehydration zone, the invention eliminates the need for a separate relatively expensive nylon carrier pad like in some prior devices.

The present dehydration sensor allows one to accurately monitor either quantitatively or semi-quantitatively the specific gravity of urine. The sensor includes a porous substrate, with a buffered ink system that is directly deposited on a portion of the substrate. The substrate forms part of a buffering pad. The buffered ink system is composed of either a) 0.5-30 wt. % of a weak polymeric acid or b) 0.5-10 wt. % of a weak polymeric base, or c) a combination of 0.5-30 wt. % of the weak polymeric acid and 0.5-10 wt. % of the polymeric base, 0.5-70 wt. % of a polymeric stabilizer, which functions as a proton-exchange hydrogen-bonding neutral buffer bridge, and a surfactant, and a pH-sensitive dye.

Alternatively, the percentage of weak polymeric acid and weak polymeric base present can range from about 0.5 wt. % to about 25 wt. %, and between about 0.5 wt. % and about 7 wt. % or 8 wt. %, respectively. Typically, the percentage of weak acid is between about 1% and 15% or 20%, and percentage of weak base is between about 1% and 4% or 5%. The amount of polymeric stabilizer or proton-exchange hydrogen-boding neutral buffer bridge can range from about 0.5 wt. % to about 60 wt. %. Typically, the amount of polymeric stabilizer is between about 1 wt. % or 3 wt. % and about 40 wt. % or 50 wt. %; more typically, the percentage is between about 5 wt. % or 7 wt. % and 30 wt. % or 35 wt. %, or preferably from about 0.5 wt. % to about 25 wt. %, inclusive.

According to the invention, the polymeric base can be, for instance, poly(allylamine), poly(ethyleneimine), poly(vinylamine hydrochloride), or a combination thereof. The polymeric acid can be one or a combination of the following: poly(acrylic acid), poly(methylvinylether-alt-maleic acid), poly(4-styrenesulfunic acid-co-maleic acid), or poly(methylvinylether-alt-maleic anhydride). The polymeric stabilizers can be, for example, a polyvinyl alcohol or a polyethylene oxide.

The pH-sensitive dye employed in the dehydration sensor can be, for example, any one of the following, but is not limited to these dyes: bromocresol green, bromothymol blue, nitrazine yellow, meta-cresol purple, thymol blue, xylenol blue, cresol red, bromophenol blue, congo red, methyl orange, bromochlorophenol blue, ethyl orange, chrysoidin, methyl red, alizarin red S, cochineal, chlorophenol red, bromocresol purple, para-nitrophenol, alizarin, brilliant yellow, neutral red, rosolic acid, phenol red, meta-nitrophenol, or a combination of these dyes.

According to the invention, the cationic polymeric surfactant serves as an immobilizer of the pH-sensitive dye onto the substrate, so that the dyes would not leach from the area applied on the substrate. The surfactant has an ionic charge opposite from the pH-sensitive indicator. Since the immobilizer is a surfactant, it also increases the general wettability of the formulation. Examples of these agents may include: SSB-6 (poly[acrylic acid-co-butyl acrylate-co-2-ethylhexylacrylate-co-sodium-2-acrylamidopropane sulfonate]) or OASIS "L7170" (poly[methyl acrylate-co-[(2-acryloyloxy)ethyl]trimethyl ammonium chloride]). The amount of cationic polymeric surfactant should be similar to the percentage of pH indicator, since the surfactant is to immobilize the indicator, typically, in a ratio of indicator:surfactant of from about 5:1, 5:2 or 5:3 to about 1:1.

SECTION I

LATERAL FLOW FORMAT

Lateral flow-based diagnostic device for immunoassays have been well accepted and widely used as consumer diagnostic products for such functions as pregnancy tests. The present invention pertains to, in part, an assay apparatus that monitors specific gravity of a urine sample. Even though superficially similar in terms of its user-friendliness and costs, the present hydration measuring device is totally different from traditional immunoassay technologies in terms of the chemistry and mechanisms for signal generation. FIG. 1 shows a schematic illustration of the format of the various parts of a typical lateral flow assay device 10. Typically, the lateral flow strip is made from a porous matrix 12 that is arranged to be in fluid communication between the various regions of the assay device, namely: a sampling zone 14, a buffer pad 16, a detection zone 18 and a control zone 20. The sampling zone is the area where a sample is deposited. The buffer pad is loaded diffusively with buffer components which changes its pH once exposed to samples of different ion concentrations. The buffer pad can have a wicking pad. The buffer pad has a detection zone that has a pH indicator which exhibits a color change responding to different pH levels. The detection zone is loaded with a pH indicator that can detect the pH change of the buffer and the control zone detects the presence of the samples for the whole device. In some embodiments, a sample observation or feedback zone has a non-diffusively immobilized pH indicator and pH adjuster. The pH indicator exhibits a color transition upon contact with a urine sample.

A representative description of color chemistry for ion strength measurement of urine is shown in the following reaction mechanism of color change in detection zone by weak acid dissociation according to the invention.

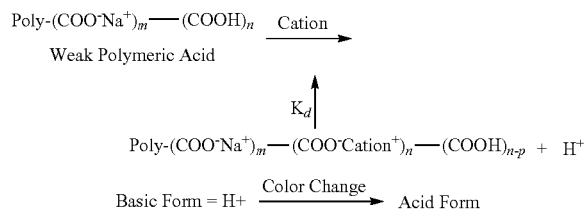

Weak polymeric acids or bases change their apparent association or dissociation constants with a change in the ion strength of test environment. For instance, when cation concentrations increase from a sample, the dissociation constant of a carboxylic acid-based weak acid increases to release more protons and increases the acidity of the solution. A pH indicator can detect change in acidity and change color. Examples of useful pH indicators may include bromothymol blue, bromophenol blue, phenol red, neutral red, methyl orange, and alizine yellow R.

An important criterion for selecting a color indicator in the detection zone is its sensitivity towards subtle pH change of the buffer caused by the ion strength of urine. Given that the pH of normal urine is neutral, the indicator preferably has a significant color transition at around pH of about 7±2, such as thymol blue and bromothymol blue. The initial color of the immobilized indicator can be easily adjusted by depositing the indicator along with a pH adjuster, either an acid, a buffer, a base, or a combination of these. It is important that the initial color can provide a sharp color contrast. For instance, when bromothymol blue is used as an indicator, alkaline conditions cause the detection zone to manifest a vivid green color, which is clearly distinguishable from a yellow color when under acidic conditions.

The control zone is a simple mechanism that can assure users that enough of a sample has been applied to the assay device in a correct manner and that the sample has been in contact with the reagents in the detection zone. A color-forming control signal is developed on the assay device downstream from the detection zone. The color development chemistry involves a pH indicator immobilized in the area of the control zone along with a pH adjuster to generate an initial pH value in the range of normal urine (i.e., 5-10). The pH indicator presents an initial color, which once a urine sample passes through the detection zone and migrates into the control zone, the pH around the control zone will change and induce a color change for the control indicator. This signals that sufficient sample has passed from the detection zone and the test is done correctly.

SECTION II

DEHYDRATION SENSOR FORMAT

For a dehydration sensor or indicator to be directly incorporated into a personal care product, the sensor should satisfy a number of requirements. These requirements include: a) the sensor should have a longer reading time window of at least six hours or more; b) the sensor should be simple and easy to read or interpret; c) the sensor and product should be able to tolerate multiple wet insults; d) the sensor should be able to be incorporated into existing personal-care products with minimal modification to the product or its manufacturing process, and e) the sensor and product should be relatively inexpensive to make at minimal cost. Urine reagent strips which change color based on urine ionic strength are commercially available, but they are not applicable for personal care products due to their dye diffusion and color instability issues. Recently, we have developed dehydration sensors that overcame these issues and can potentially used as insert for personal garment. However, the sensor design and manufacture steps are quite complicated. The present invention discloses a dehydration sensor that can be implemented in an ink form.

Previous generations of dehydration indicators are embodied by a buffered substrate (e.g., cellulose pad), a nylon membrane upon which is immobilized pH dye(s) for a detection zone, a laminate to adhere the detection zone to the substrate and optionally a surfactant, such as described in U.S. patent application Ser. Nos. 12/338,673, or 12/338,636, the contents of which are incorporated herein by reference. Alternatively, one may dispense with the nylon membrane and immobilize the pH-sensitive dye to the buffered cellulose pad of the substrate. These kinds of sensors used a lateral-flow based assay in which urine travels up a test strip and directly contact a detection zone. The mechanism of detection is based on the fact that weak polymeric acids and bases change their apparent association/dissociation constants with a change in the ionic strength of a medium, which causes a change in relative pH. The shift can be detected using a colorimetric change of a pH dye. The ionic strength of the urine (which corresponds to the hydration level of the user) shifts the pH of the buffer, which can be measured with a pH dye that is contained in the detection pad.

The present invention according to one aspect involves a dehydration sensor that incorporates a pH-sensitive dye that is combined with a weak polymeric acid buffer (e.g., polyacrylic acid, etc.) which can release protons when it encounters an ionic solution, such as urine. The inventive sensor can use a less amount of dye or buffer material than prior forms and can generate better buffering activity.

The present invention describes an ink-based approach for dehydration indicators that enhance signal stability and is simpler to manufacture. The invention builds upon previous work that integrated lateral-flow based dehydration indicators into absorbent personal care products. The present invention, however, adds or improves the functionality and overcomes some problems and disadvantages associated with previous sensors. For instance, with prior indicator embodiments, one had a problem with bleeding and/or leaching of dyes from the target area or active site of the sensor substrate. Further, in prior generations, the indicator required a cellulosic pad that is entirely pre-treated with buffer solution and dried prior to the printing of a pH-sensitive dye.

In prior generations of dehydration sensors, the indicator required a porous cellulosic pad that is entirely pre-treated with buffer solution and allowed to dry before addition of a dye. In the present invention, we demonstrate that the buffering capacity of the indicator would be significantly enhanced by means of a polymeric acid-polymeric base formulation. Due to the enhanced buffering capacity, one no longer need to pre-treat the entire cellulosic pad with buffer solution. Instead, the physical dimensions of the buffer area or portion of the cellulosic pad can be significantly reduced to enable one to easily print or stripe the indicator pad. According to this approach, the buffer zone can be deposited or printed downstream from a dye-containing area or zone on the assay substrate such as illustrated in FIG. 3A. Alternatively, both the buffer and dye reagents can be applied one over the other within the same physical area or zone as shown in FIG. 3B.

In the first embodiment shown in FIG. 3A, the dye and buffer are placed at the different locations on the substrate. An example of a formulated dye solution (10% polyvinyl alcohol, 5 mg/ml bromothymol blue and poly-surfactant oasis in 50:5:2 ratio, 4 microliter) is placed on a 25 mm×5 mm strip. The buffer solution (10% polyvinyl alcohol, 45 mg/ml polyacrylic acid and 20% polyallylamine in 20:20:3 volume ratio, 8 microliter) is then placed right below the dye spot on the substrate to form the sensor strip. The strip is dried at 50° C. for 30 minutes. 100 microliter of synthetic urine with varying ionic strength was placed at the end of the sensor strips close to the buffer end. Changes in color are observed to be responsive to synthetic urine with the different USG levels. In the second embodiment shown in FIG. 3B, the dye and buffer are placed at the same location on a substrate. An example of the formulated dye solution (10% polyvinyl alcohol, 5 mg/ml bromothymol blue and poly-surfactant oasis in 50:5:2 ratio, 3 microliter) is first placed on a cellulosic substrate 5 mm×5 mm. The buffer solution (10% polyvinyl alcohol, 45 mg/ml polyacrylic acid and 20% polyallylamine in 20:20:3 volume ratio, 2 microliter) is then placed on the same place on the substrate to form the sensor. The sensor pieces are dried at 50° C. for 30 minutes. A series of 25 microliter samples of synthetic urine, each with different ionic strength, is put on to the sensor piece. Observed color changes are responsive to synthetic urine with the different USG levels.

In contrast, the present device demonstrates that by using a unique buffer formulation, the buffer capacity of the indicator can be enhanced. Due to this enhanced buffer capacity, one no longer needs to treat the entire cellulosic pad with buffer solution. Instead, the buffer position can be significantly reduced in area or to a quantity that can be more easily printed to striped on an indicator pad. According to this approach, the buffer zone can be printed below a dye zone or both buffer and dye can be printed in the same physical area of a zone. Furthermore, the pH-sensitive dye is immobilized so that the buffered inks will not leach or contaminate secondary areas of personal care product.

The buffer's pH experiences change with different ion concentrations or ion strengths or specific gravity of a sample. The buffer may consist of partially neutralized weak polymeric acid or base. Examples of weak polymeric acids or bases include poly(acrylic acid), poly(maleic acid), poly(vinylamine) and poly(4-vinylpyridine). The buffer may consist of non-polymeric weak acids such as 2-(N-morpholino)-ethanesulfonic acid and bis-(aminoethyl)-glycol ether N,N,N',N'-tetraacetic acid. The buffer components may or may not permanently be immobilized on the porous matrix. Examples of porous matrices include cellulose pads, filter papers, non-woven materials and glass fibers pads.

The porous matrix should not interfere significantly with the association and dissociation constant of the buffer. The dehydration test device has a test pad (zone) that non-diffusively immobilizes with a pH indicator. The pH indicator desirably exhibits a color transition around neutral pH, or at a pH from about 5.5 to about 10.5. Examples of the pH indicator include bromothymol blue, thymol blue, m-cresol purple, brilliant yellow and neutral red. The matrix is preferred to be porous and urine (aqueous) friendly to allow rapid penetration of urine.

The dehydration sensor device has a porous and hydrophilic wicking pad. The wicking pad is preferred to have a relatively high or significant absorbent capacity of holding fluids, such as water or urine. The dehydration test device has a feedback or control zone as part of a wicking pad. The control zone can change color upon contact with urine regardless of the pH and/or specific gravity of the urine sample. The wicking pad can have a non-diffusively immobilized pH indicator and a pH adjuster on a porous and water/urine friendly matrix. The pH indicator can exhibit a color transition at a pH either less than about 5.5 or greater than about 10.5. Examples of the pH indicator include bromophenol blue, bromochlorophenol blue, phloxine B, Bromocresol green and Congo red. Examples of the pH adjuster include citric acid, oxalic acid and tartaric acid. The matrix is preferred to be porous and urine friendly to allow rapid penetration of urine.

In particular embodiments, the buffer components can be selected from a weak polymeric acid, such as poly(acrylic acid) (MW: 3,000-60,000); poly(methylvinylether-alt-maleic acid) (80,000-960,000); poly(4-styrenesulfunic acid-co-maleic acid) (MW: 20,000); or poly(methylvinylether-alt-maleic anhydride) (MW: 80,000). The weak polymeric base can be: poly(allylamine) (MW: 1,000-60,000), poly(ethyleneimine) (MW: 1,800-10,000), poly(vinylamine hydrochloride) (MW: 25,000). For instance, the dehydration sensor incorporates pH sensitive dye, such as bromothymol blue, and multi-components buffer (e.g. polyacrylic acid and polyallylamine).

The location of the pH sensitive dye and multi-components buffer can be the same or different. Upon contacting with urine, the ions in urine trigger the buffer to release protons and cause the pH sensitive dye on the sensor to change color. The degree of color change depends on the urine ionic strength.

Figure 4A:
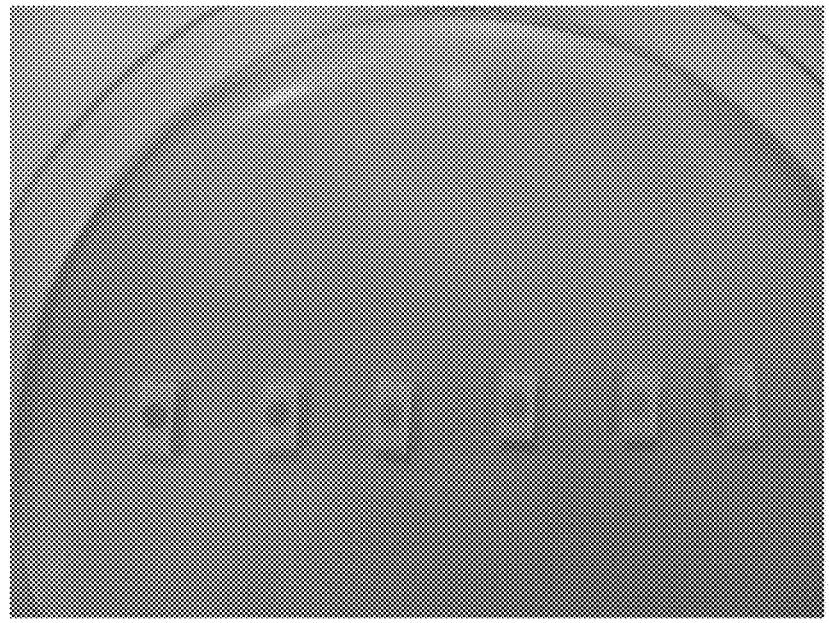
FIGS. 4A-4G are a series of photographic images of spots on cellulosic substrates printed with pH-indicating ink, according to the present invention. The dehydration sensors shown in FIGS. 4A-4G in the series are prepared according to different ratio of pH components, as indicated in each sample.
Figure 4B:
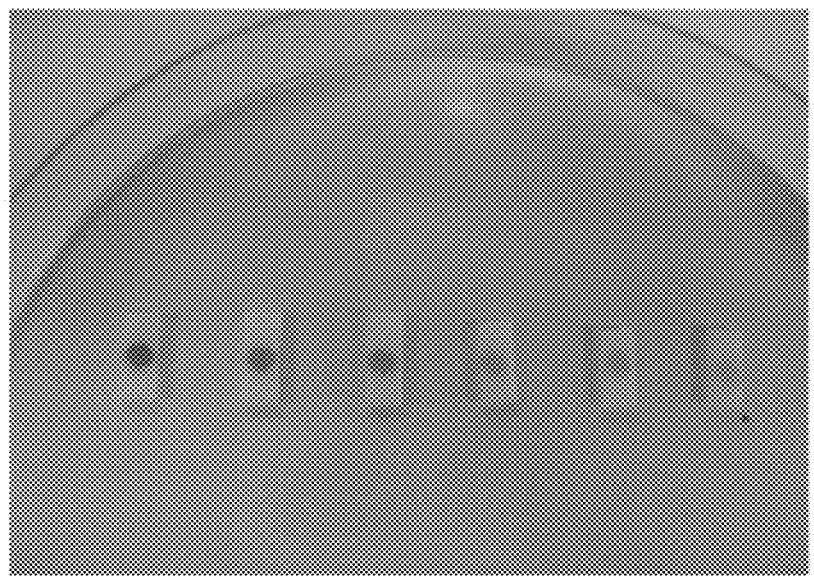
Figure 4C:
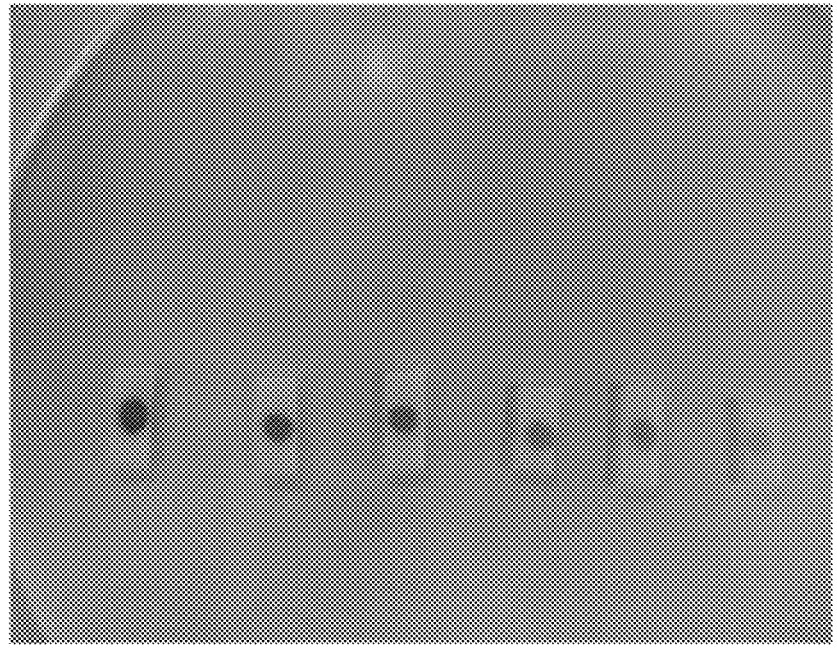
Figure 4D:
Figure 4E:
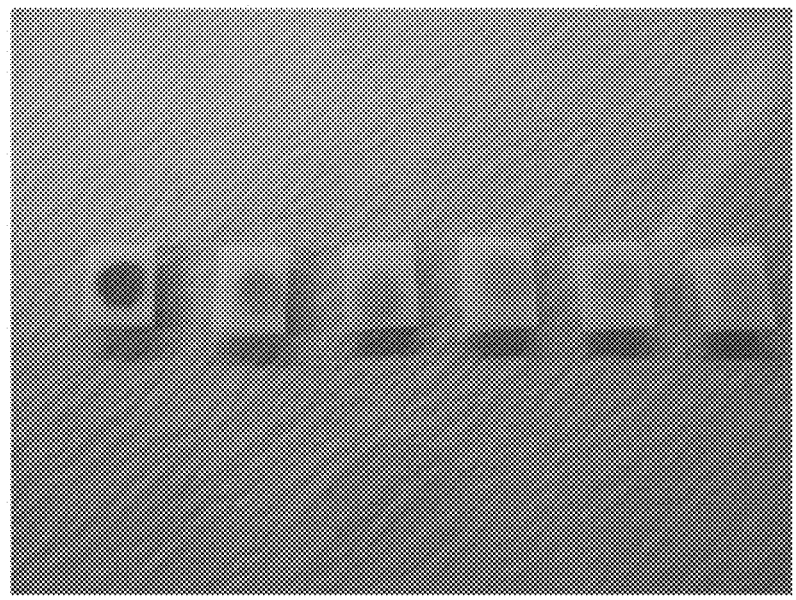
Figure 4F:
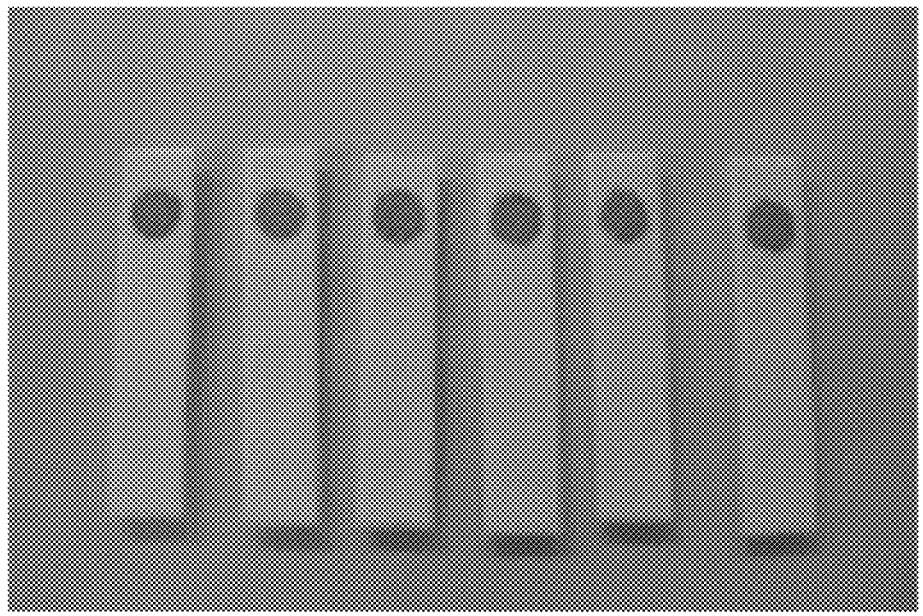
Figure 4G:
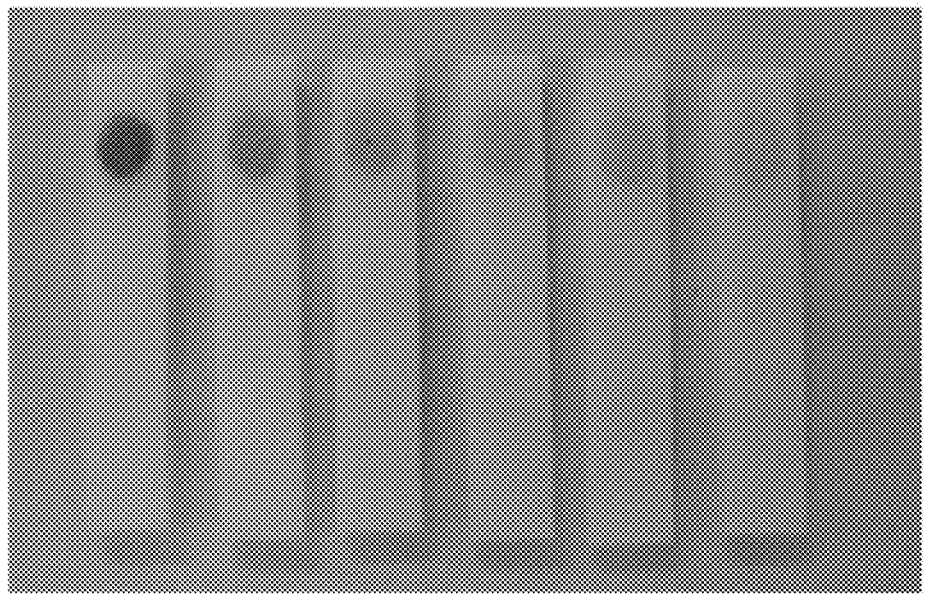

According to a method of monitoring dehydration by testing for the ion strength of a urine sample, one can provide a lateral flow strip with a porous matrix in fluid communication with a buffer pad, wicking pad, and a flow-rate control zone situated between said buffer pad and wicking pad; introduce a test sample to a sample zone on said buffer pad, allow the sample to interact at a detection zone which can be immediately next to the sample deposit zone. FIG. 4, represents the sensitivity and effectiveness of dehydration sensors according to the present invention. Six samples with ion-concentrations ranging from 1.004 to 1.035 are tested. The corresponding photographic image of these sensors is shown in FIG. 4G, in which the color change by the pH indicator is more apparent.

In some embodiments, a flow-rate control zone is situated downstream from the detection zone, and the urine seeps to the flow-rate control zone before developing a visual signal in a control zone of the wicking pad. The flow-rate control zone can regulate the flow rate by means of manipulating porosity, density, or ion affinity gradient in a matrix forming at least part of said flow-rate control zone.

According to the invention, by increasing the polymeric base (polymeric amines) content, the color transition greatly shifts. The incorporation of a weak polymeric base component enables one to more precisely control the buffer range capacity and allows one to use a smaller more targeted volume of buffer ink components in the present device. (e.g., 0.1-10 microliters 0.5-5 or 7, 1-3 or 4 microliters), small discrete areas on the substrate no need to coat the entire substrate. This leads to a cost savings and an overall simpler device to fabricate. This affords an advantage that one can minimized the active area of the detection zone.

Particular uses for the present invention, it is envisioned, may include a dehydration test sensor designed for inclusion in an absorbent article, such as a diaper, adult incontinence product, or other personal care garment, where precise, continuous monitoring of the test is not practical. For a dehydration indicator, the detection zone requires 5-10 minutes to stabilize and reach equilibrium after coming in contact with the urine sample. If the test is read prior to equilibrium, inaccurate results may be given. Thus, it would be useful to include one of these flow-rate control zones in between the detection zone and the sample observation-control zone such that the sample fluid would not react with the sample observation-control zone until 10 minutes after reaching the detection zone. In such an embodiment, the user would be assured that the test is ready to read once the observation-control zone color has formed. The flow-rate control zones could also be used in between detection zones of a multi-analyte test in which the signal from the zones forms at different rates. In such situation, it would be advantageous that most or all of the signals develop at the same time, so as not to confuse the user. Otherwise, the user may assume the test is complete once one signal is formed and therefore miss the other signals that develop later.

In another aspect, the invention also relates to a method for testing specific gravity of a urine sample, the method comprises: introducing a urine sample to a sample zone, passing said urine through a buffer pad in a detection zone, causing a color change in a pH indicator in said detection zone, passing the urine through a flow-rate control zone to regulate the appearance of a visual signal in an observation-feedback zone of the wicking pad (for a predetermined interval), until a color transition in the detection zone attains color stability.

The testing is normally performed according to the following: A urine sample is introduced into the sample zone and flows through the buffer zone through capillary action. The ions in the urine cause the change of the buffer's pH in the buffer pad. Some of the samples flows into the detection zone where the pH indicator will show different colors depending upon the pH of the buffer, which is determined by the ion concentration of the urine sample. It is the color of the detection zone that correlates with the urine ion strength, or specific gravity of the urine, which reflects a person's hydration status. It was found that the color signals in the detection zone normally take some time (e.g., normally 10 to 30 minutes depending upon the device dimension and configuration) to be fully developed. Some of the sample further flows to the flow-rate control zone, then to the wicking zone, and then to the sample observation-control zone to finally trigger a color change in the reading zone. The time it takes for the sample to fully reach the observation-feedback zone to develop the feedback signal can be easily regulated through many parameters of the flow-rate control zone, including the selection of the material, width and length of the zone and pore size. The color change in the control zone of the wicking pad can be used to provide not only assurance that the test is properly done, but also to ensure a minimal time that the sample has contacted with the detection zone before reading the signal. For instance, the test is not valid if the feedback pad has not experience a color change, indicating that one either did not have sufficient amount of sample introduced or had not allowed sufficient time for the signal to develop in the detection zone.

SECTION III

EMPIRICAL EXAMPLES

Substrate:
Cellulose Fiber Pads (Millipore CFSP223000, 20 cm×30 cm sheets) from Millipore Corporation (Bedford, Mass., USA) are used as the substrate. The substrate is made into 25 mm×5 mm strips when indicator's buffer and dye zones were separated, and 5 mm×5 mm strips were used when the buffer and dye were printed in the same zone on the cellulosic pad.

Buffer Formulation:
The buffer formulation consisted of the following reagents unless otherwise specified: polyvinylalcohol (PVOH): 10% solution in DI $H_2O$, polyacrylic acid (PAH): 45 mg/mL in DI $H_2O$, and either polyallylamine (PAA) or polyethyleneimine (PEI): 20% solution in DI $H_2O$ pH Dye Formulation:
The dye formulation consisted of the following reagents unless otherwise specified: polyvinylalcohol (PVOH): 10% solution in DI $H_2O$, bromothymol blue (BTB): 5 mg/mL in 7:3 $H_2O$/ethanol, and Oasis (PS) stock solution.

Indicator Preparation:
When the buffer zone and dye zone are separated, the preparation is as follows unless otherwise specified: The dye formulation (4 µL of 50:5:2 PVOH:BTB:PS volume ratio solution) was placed on the cellulosic substrate pad (25 mm×5 mm). The buffer formulation (8 µL of 20:20:3 PVOH:PAH:PAA volume ratio solution) was placed right below the dye zone on the substrate to form the indicator. The indicator was dried at 50° C. for 30 minutes.

When the buffer and dye are printed in the same zone on the indicator, the preparation is as follows unless otherwise specified: The dye formulation (3 µL of 50:5:2 PVOH:BTB:PS volume ratio solution) was placed on the cellulosic substrate pad (5 mm×5 mm). The buffer formulation (2 µL of 20:20:3 PVOH:PAH:PAA volume ratio solution) was immediately placed in the same zone on the substrate. The indicator was dried at room temperature for at least 30 minutes before use.

Stability Testing for Indicator:
The indicators were prepared with the dye (3 µL of 50:5:2 PVOH:BTB:PS volume ratio solution) and buffer (2 µL of 10:15:1 PVOH:PAH:PEI volume ratio solution) printed in the same zone. The indicators were stored in a plastic sealable bag in the light, a plastic sealable bag in the dark, and an aluminum pouch in the dark. The color intensity of the indicators was monitored using a Minolta CM-2600d spectrophotometer over 30 days. The stability experiments were conducted in triplicate.

Example 1

A 2 cm×30 cm piece of cellulosic substrate is prepared and printed with an ink formulation according to the present invention. The dye and buffer are placed at the same location on the substrate. The dye solution (10% polyvinyl alcohol, 5 mg/ml bromothymol blue and poly-surfactant oasis in 50:5:2 ratio, 3 microliter) was first placed on a cellulosic substrate 5 mm×5 mm. The buffer solution (10% polyvinyl alcohol, 45 mg/ml polyacrylic acid and 20% polyallylamine in 20:20:3 volume ratio, 2 microliter) was then deposited over the dye solution in the same location on the substrate to form a sensor. The sensor substrate is allowed to air dry in ambient conditions and cut into separate pieces, and tested against synthetic urine with different specific gravity (USG) values. Each of the pieces in the set of samples 1-5 were processed under similar conditions, but with different ratios of polyacid and polybase.

As shown in the accompanying FIGS. 4A-4E, photographic images of each sample set illustrates the results after treating the sensors with synthetic urine. The sensor pieces manifest a range of different colors and shades to reflective of the different USG values.

Example 2

The substrate was prepared in a similar fashion as in Example 1, but the dye and buffer are deposited at different locations along the substrate. The formulated dye solution (10% polyvinyl alcohol, 5 mg/ml bromothymol blue and poly-surfactant oasis in 50:5:2 ratio, 4 microliter) was placed on a 25 mm×5 mm strip. The buffer solution (10% polyvinyl alcohol, 45 mg/ml polyacrylic acid and 20% polyallylamine in 20:20:3 volume ratio, 8 microliter) was then placed below to the dye spot on the substrate, as viewed in the accompanying images, to form the sensor strip. The sensor pieces were allowed to air dry, separated, and tested against synthetic urine with different USG values. The ink spots in the set of sensor pieces in sample 6, PVOH:Polyacid:Polybase (6.4:1.5:1), appears greenish before application of the synthetic urine samples. Similar to that observed in FIGS. 4A-4E, the individual sensor pieces developed a spectrum of color that clearly differentiates the different USG values after they were treated with the urine samples.

Table 1, summarizes the results for the set of sensor pieces in samples 1-6, from both Examples 1 and 2. Associated FIG. 4 illustrates in gray-scale the gradation in appearance in the sensor for each of the different USG values applied.

TABLE 1

| Sample Examples: Wt. % Ratio | USG = 1.002 | USG = 1.008 | USG = 1.014 | USG = 1.020 | USG = 1.025 | USG = 1.035 | FIG. |
|---|---|---|---|---|---|---|---|
| Ex. 1 PVOH:Polyacid:polybase Poly(ethyleneimine) 65:20:1 | Green | Green-Yellow | Yellow | Yellow | Yellow | Yellow | 4A |
| Ex. 2 PVOH:Polyacid:polybase Poly(ethyleneimine) 45:15:1 | Blue | Blue-Green | Green | Yellow | Yellow | Yellow | 4B |
| Ex. 3 PVOH:Polyacid:polybase Poly(ethyleneimine) 25:5:1 | Blue | Lighter Blue | Blue-Green | Green | Green-Yellow | Yellow | 4C |
| Ex. 4 PVOH:Polyacid:Polybase 0:15:1 | Green | Green-Yellow | Yellow | Yellow | Yellow | Yellow | 4D |
| Ex. 5 PVOH:Polyacid:polybase Poly(allyamine) 13:1.5:1 | Blue | Green | Green Yellow | Yellow | Yellow | Yellow | 4E |
| Ex. 6 PVOH:Polyacid:polybase Poly(allyamine) 6.4:1.5:1 | Blue | Blue-Green | Green | Yellow | Yellow | Yellow | 4F (before) 4G (after) |

The present invention has been described both generally and in detail by way of examples and the figures. Persons skilled in the art, however, can appreciate that the invention is not limited necessarily to the embodiments specifically disclosed, but that substitutions, modifications, and variations may be made to the present invention and its uses without departing from the spirit and scope of the invention. Therefore, changes should be construed as included herein unless the modifications otherwise depart from the scope of the present invention as defined in the following claims.

We claim:
1. A dehydration sensor that comprises:
a porous substrate, with a buffered ink system that is directly deposited on a portion of said substrate;
the buffered ink system is composed of 0.5-30 wt. % of a weak polymeric acid, 0.5 -3 wt. % of a polymeric stabilizer which functions as a proton-exchange hydrogen-bonding neutral buffer bridge, and a cationic surfactant; and
a pH-sensitive dye;
wherein said surfactant serves as an immobilization agent of the pH-sensitive dye and buffered ink system.
2. The dehydration sensor according to claim 1, wherein said polymeric acid is one or a combination of the following: poly(acrylic acid), poly(methylvinylether-alt-maleic acid), poly(4-styrenesulfunic acid-co-maleic acid), or poly(methylvinylether-alt-maleic anhydride).
3. The dehydration sensor according to claim 1, wherein said polymeric stabilizers is: a polyvinyl alcohol or a polyethylene oxide.
4. The dehydration sensor according to claim 1, wherein said substrate is a polyester, cellulosic material, or rayon.
5. The dehydration sensor according to claim 1, wherein buffered ink system is deposited in the same zone on said substrate as said pH-sensitive dye is deposited.
6. The dehydration sensor according to claim 1, wherein said buffered ink system is deposited in separate zones from said pH-sensitive dye.
7. The dehydration sensor according to claim 1, wherein said proton-exchange hydrogen bonding neutral buffer bridge that facilitates an exchange of protons between components of said buffer ink system, and protects said sensor from $CO_2$-induced degradation.
8. The dehydration sensor according to claim 1, wherein said proton-exchange hydrogen bonding neutral buffer bridge is a polyvinyl alcohol or a polyethylene oxide.
9. The dehydration sensor according to claim 1, wherein said pH-sensitive dye exhibits a color transition at a pH from about 5.5 to about 10.5.
10. The dehydration sensor according to claim 1, wherein said pH-sensitive dye is one of the following: bromocresol green, bromothymol blue, nitrazine yellow, meta-cresol purple, thymol blue, xylenol blue, cresol red, bromophenol blue, congo red, methyl orange, bromochlorophenol blue, ethyl orange, chrysoidin, methyl red, alizarin red S, cochineal, chlorophenol red, bromocresol purple, para-nitrophenol, alizarin, brilliant yellow, neutral red, rosolic acid, phenol red, meta-nitrophenol, or a combination thereof.

11. An absorbent article comprising:
a first, inner layer, an absorbent core, and a second, outer layer;
a lateral flow-based dehydration sensor for measuring the specific gravity of urine, said dehydration sensor has a substrate with a buffer pad;
said dehydration device is situated near an area of said inner layer that will be subjected to insult of urine, and which can be insulted either directly or by means of capillary transport;
said buffer pad has a detection zone in which is a buffered ink system that is directly deposited on said buffer pad;
said buffered ink system is composed of 0.5-30 wt. % of a weak polymeric acid, 0.5-3 wt. % of a polymeric stabilizer that functions as a proton-exchange hydrogen-bonding neutral buffer bridge, and a cationic surfactant; and a pH-sensitive dye; wherein said cationic surfactant serves as an immobilization agent of the pH-sensitive dye and buffered ink system.

12. The absorbent article according to claim 11, wherein each of said several zones is in fluidic communication with each other either directly or indirectly by an adjacent component.

13. The absorbent article according to claim 11, wherein said absorbent article is a diaper, adult incontinence product, or personal or feminine hygiene product, or absorbent pad for medical or hospital uses.

\* \* \* \* \*